(12) United States Patent
Carlyon et al.

(10) Patent No.: US 8,486,015 B2
(45) Date of Patent: Jul. 16, 2013

(54) SAFETY NEEDLE SHIELD APPARATUS

(75) Inventors: James L. Carlyon, Leadwood, MO (US); Steve Earhart, St. Louis, MO (US); Eugene E. Weilbacher, Chesterfield, MO (US)

(73) Assignee: Covidien AG (CH)

( * ) Notice: Subject to any disclaimer, the term of this patent is extended or adjusted under 35 U.S.C. 154(b) by 0 days.

(21) Appl. No.: 11/343,825

(22) Filed: Jan. 30, 2006

(65) Prior Publication Data

US 2006/0189936 A1 Aug. 24, 2006

Related U.S. Application Data

(63) Continuation of application No. 10/609,304, filed on Jun. 27, 2003, now Pat. No. 7,037,292.

(51) Int. Cl.
 *A61M 5/00* (2006.01)
(52) U.S. Cl.
 USPC .......................................... 604/110; 604/192
(58) Field of Classification Search
 USPC ............ 604/110, 181, 187, 192, 198, 164.08, 604/263
 See application file for complete search history.

(56) References Cited

U.S. PATENT DOCUMENTS

| | | |
|---|---|---|
| 4,183,246 A | 1/1980 | Reynolds |
| 4,676,783 A | 6/1987 | Jagger et al. |
| 4,747,831 A | 5/1988 | Kulli |
| 4,767,413 A * | 8/1988 | Haber et al. ................. 604/198 |
| 4,813,426 A | 3/1989 | Haber et al. |
| 4,900,307 A | 2/1990 | Kulli |
| 4,900,311 A | 2/1990 | Stern et al. |
| 4,978,343 A * | 12/1990 | Dysarz et al. ................. 604/195 |
| 5,084,030 A | 1/1992 | Byrne et al. |
| 5,085,639 A | 2/1992 | Ryan |
| 5,108,376 A | 4/1992 | Bonaldo |

(Continued)

FOREIGN PATENT DOCUMENTS

| | | |
|---|---|---|
| EP | 1 221 305 | 7/2002 |
| JP | 07506011 A | 7/1995 |
| JP | 2647132 B2 | 8/1997 |
| WO | WO 00/47256 | 8/2000 |

OTHER PUBLICATIONS

Office Action issued Nov. 11, 2011 in related Japanese Patent Application Serial No. 2006-517791, 3 pgs.

*Primary Examiner* — Kevin C Sirmons
*Assistant Examiner* — Phillip Gray
(74) *Attorney, Agent, or Firm* — Lisa E. Winsor, Esq.

(57) ABSTRACT

A safety shield apparatus is provided that includes a housing that defines a cavity. A distal end of the housing includes a cover having a movable tab. A hub is disposed for movement within the housing and includes a needle having a distal end and a movable projection. The hub is biased between an extended position, such that the distal end of the needle is exposed and the movable projection is releasably disposed with the cavity, and a retracted position whereby the distal end of the needle is disposed within the housing. The movable tab is engageable with the movable projection to release the movable projection from the cavity to facilitate movement of the hub. The distal end of the housing may define a lip that is configured to capture the distal end of the needle. The hub can define an angled distal surface to orient the needle out of axial alignment with the housing and into capture with the lip.

11 Claims, 8 Drawing Sheets

U.S. PATENT DOCUMENTS

| | | | |
|---|---|---|---|
| 5,129,884 A * | 7/1992 | Dysarz | 604/164.08 |
| 5,188,119 A | 2/1993 | Sunderland | |
| 5,211,629 A | 5/1993 | Pressly et al. | |
| 5,226,894 A | 7/1993 | Haber et al. | |
| 5,232,456 A | 8/1993 | Gonzalez | |
| 5,273,540 A | 12/1993 | Luther et al. | |
| 5,318,538 A | 6/1994 | Martin | |
| 5,338,303 A | 8/1994 | King et al. | |
| 5,368,568 A | 11/1994 | Pitts et al. | |
| 5,395,347 A | 3/1995 | Blecher et al. | |
| 5,538,508 A | 7/1996 | Steyn | |
| 5,554,130 A | 9/1996 | McDonald et al. | |
| 5,591,138 A | 1/1997 | Vaillancourt | |
| 5,695,475 A | 12/1997 | Best, Jr. et al. | |
| 5,746,215 A * | 5/1998 | Manjarrez | 600/573 |
| 5,779,679 A * | 7/1998 | Shaw | 604/158 |
| 5,879,331 A * | 3/1999 | Osterlind | 604/110 |
| 5,928,199 A | 7/1999 | Nakagami | |
| 5,964,739 A | 10/1999 | Champ | |
| 6,056,726 A | 5/2000 | Isaacson | |
| 6,080,137 A | 6/2000 | Pike | |
| 6,090,078 A | 7/2000 | Erskine | |
| 6,096,005 A * | 8/2000 | Botich et al. | 604/110 |
| 6,210,371 B1 | 4/2001 | Shaw | |
| RE37,439 E | 11/2001 | Firth et al. | |
| 6,524,276 B1 * | 2/2003 | Halseth et al. | 604/110 |
| 6,547,762 B1 * | 4/2003 | Botich et al. | 604/110 |
| 6,582,402 B1 | 6/2003 | Erskine | |
| 6,776,775 B1 * | 8/2004 | Mohammad | 604/195 |
| 6,786,875 B2 | 9/2004 | Barker et al. | |
| 6,972,002 B2 | 12/2005 | Thorne | |
| 6,976,976 B2 | 12/2005 | Doyle | |
| 7,037,292 B2 | 5/2006 | Carlyon et al. | |
| 7,300,421 B1 | 11/2007 | Lowry et al. | |
| 2003/0040717 A1 * | 2/2003 | Saulenas et al. | 604/198 |
| 2003/0078540 A1 * | 4/2003 | Saulenas et al. | 604/110 |
| 2003/0220619 A1 | 11/2003 | Polidoro et al. | |
| 2004/0193110 A1 | 9/2004 | Giambattista et al. | |
| 2007/0191783 A1 | 8/2007 | Shaw et al. | |

* cited by examiner

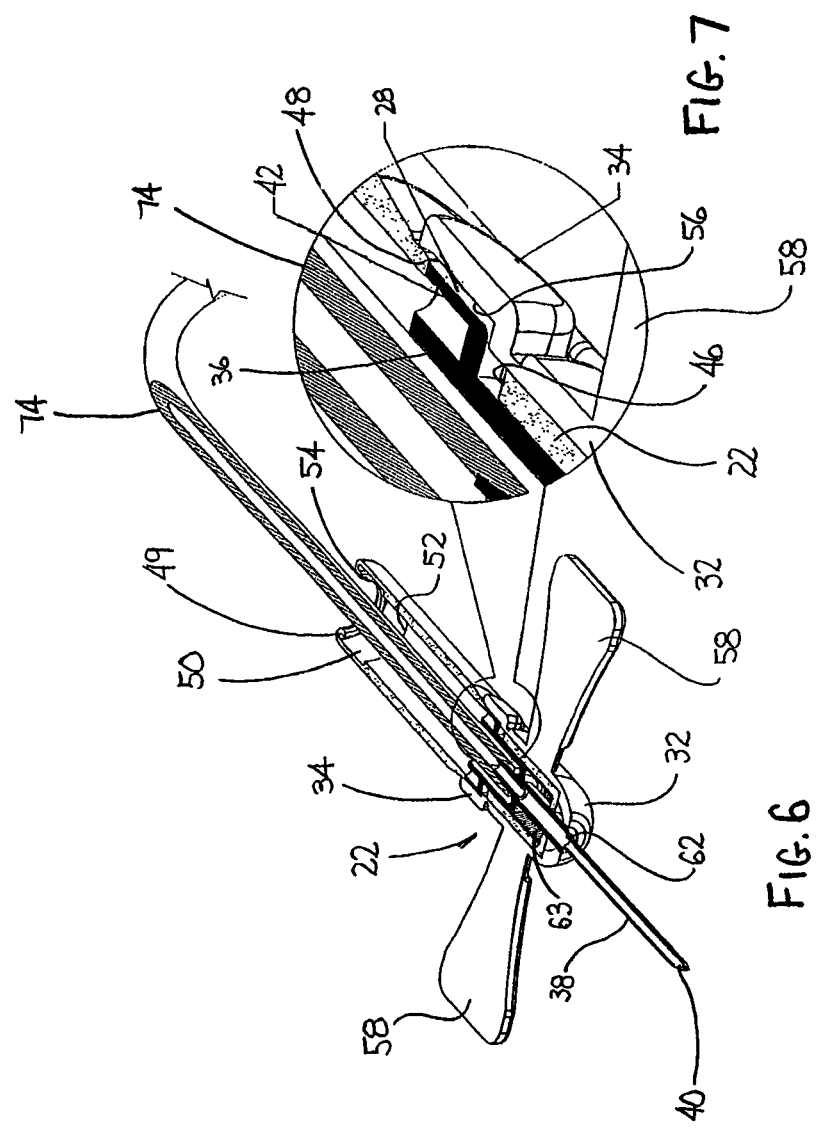

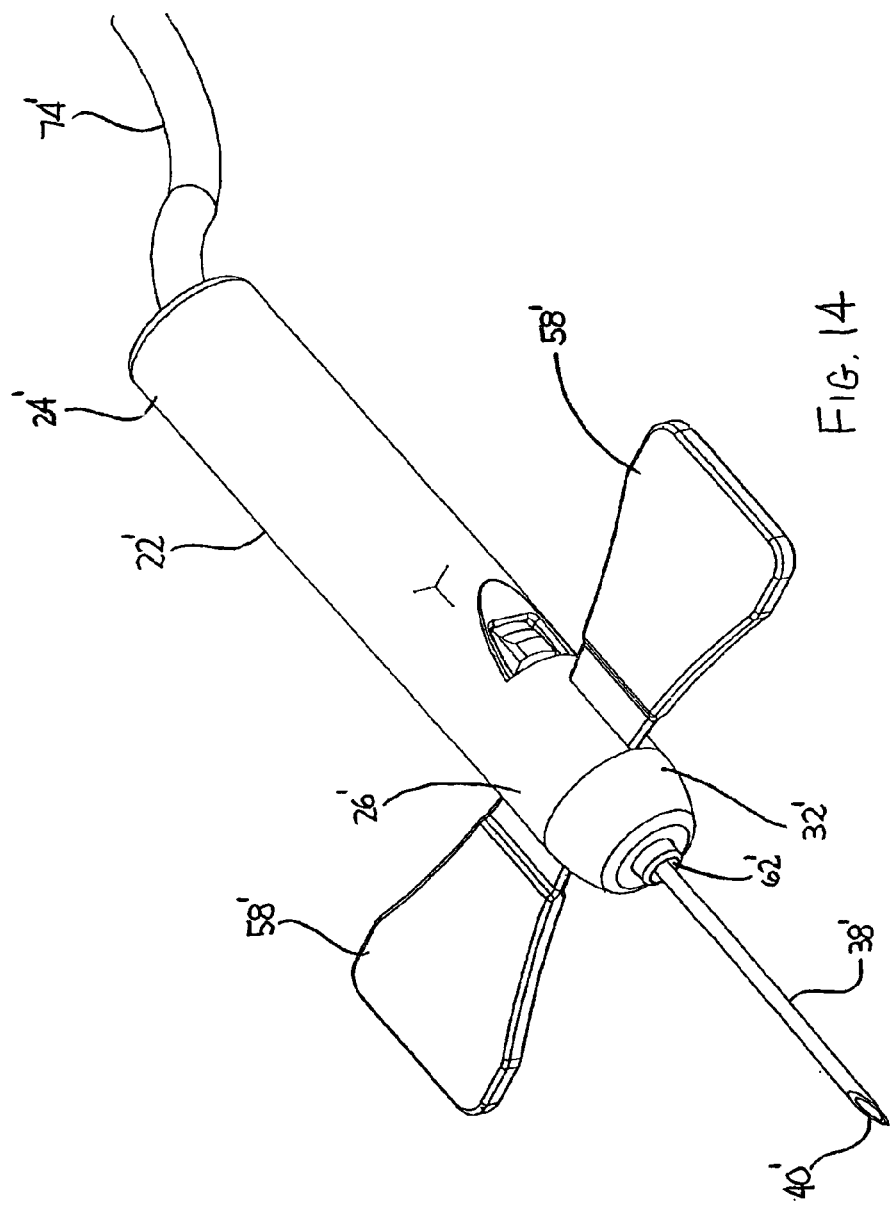

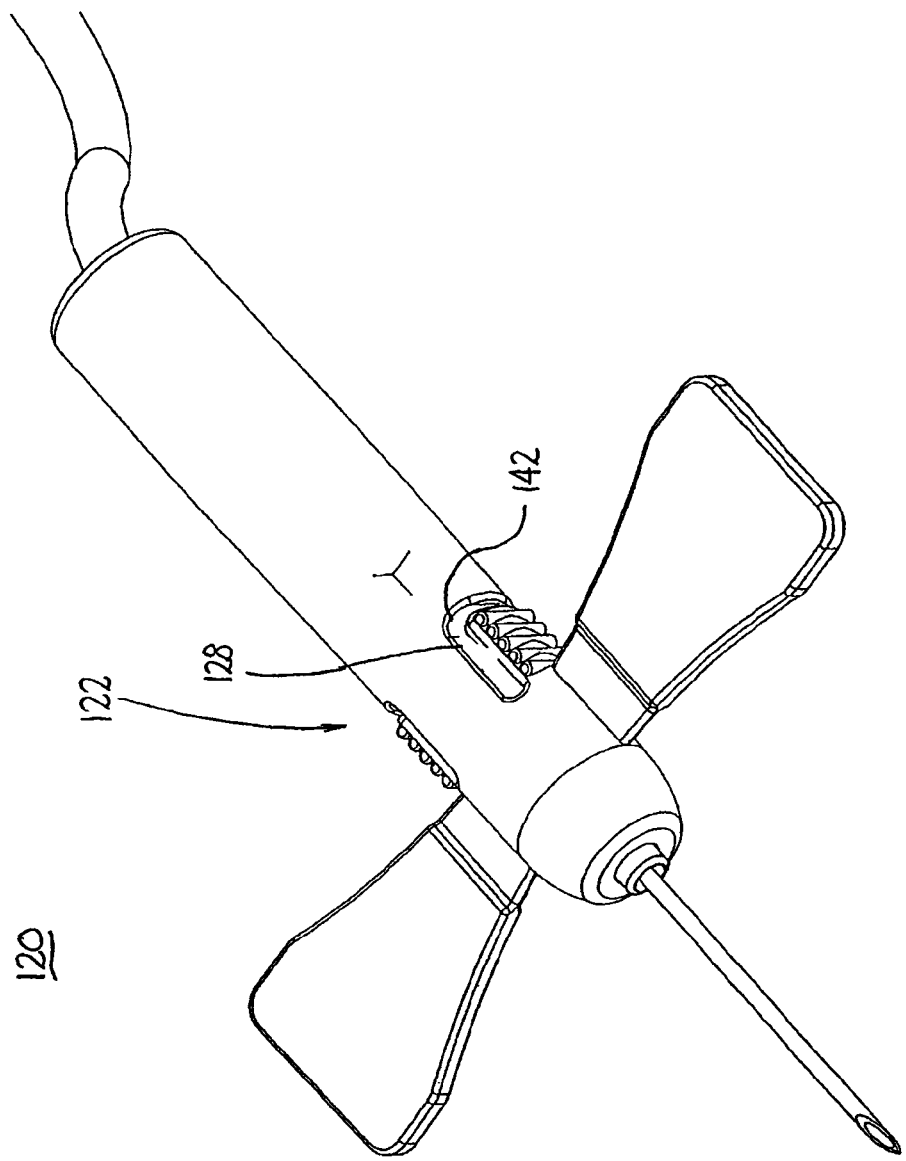

SAFETY NEEDLE SHIELD APPARATUS

CROSS REFERENCE TO RELATED APPLICATION

This patent application is a continuation of U.S. patent application Ser. No. 10/609,304 filed Jun. 27, 2003 now U.S. Pat. No. 7,037,292 which is incorporated herein in its entirety by reference.

BACKGROUND

1. Technical Field

The present disclosure generally relates to the field of medical needle assemblies for the administration of fluids, and more particularly, to safety shields that prevent hazardous exposure to a needle.

2. Description of the Related Art

Problems associated with inadvertent needlesticks are well known in the art of fluid administration, which includes fluid sampling, percutaneous medication injection and other medical procedures involving the use of medical needles. Significant attention is focused on health risks associated with hazardous needle exposure due to the contemporary sensitivity of exposure to AIDS, Hepatitis and other blood-borne pathogens. These risks are some of the most prevalent occupational health hazards among health care professionals. These professionals are in danger of contracting such blood-borne pathogens from infected patients by inadvertent needlesticks from a contaminated needle employed during medical, dental, laboratory, etc. procedures.

In an exemplary needle application, a winged intravenous assembly is employed whereby a patient receives intravenous delivery of a fluid or a fluid collection procedure is performed. A needle is connected through a winged body of the assembly to an intravenous tube. The wings are used to manipulate the assembly during insertion and withdrawal of the needle from the patient. The wings are also used to stabilize the assembly against the patient, by providing a surface area for taping, attachment, etc. to the patient to prevent movement of the assembly. The winged intravenous assembly must be withdrawn from the patient and disposed of without creating a risk of needlesticks to medical personnel. Winged intravenous needle assemblies can include winged blood collection needles, winged infusion needles, winged hemodialysis needles and blood collection bags with attached winged needles.

Attempts to overcome health hazards associated with inadvertent or undesired needlestick from a contaminated needle have produced a variety of shielding devices. Some of these devices utilize a separate shielding cap mounted over the needle after use, while other devices employ pivoting shields, extensible shields, etc. These devices may disadvantageously require the practitioner to use both hands to implement their protective components. These designs can also be relatively complicated and time consuming in use. Other such devices can require lever activation or manipulative actuation, which is prone to accidental engagement resulting in hazardous needle exposure. Further, these devices may not provide uniform and reliable motion as the protective member may jam or move offline, resulting in faulty operation and a dangerous condition to the practitioner.

Various shielding arrangements have been developed to overcome the above mentioned disadvantages. See for example, U.S. Pat. Nos. 5,108,376, 5,085,639, 4,676,783, 5,799,679, 5,928,199. These types of shielding arrangements, however, may still disadvantageously require the use of two hands to move the shield over the contaminated needle. These types of structures can also be prone to unreliable motion due to their complicated arrangements. Another drawback is that these types of devices also require complicated molds from manufacturers resulting in high production costs.

Therefore, it would be desirable to overcome the disadvantages and drawbacks of the prior art with a safety shield apparatus that reduces the occurrence of contaminated needlestick injuries and reduces exposure to pathogens. It would be desirable if the safety shield apparatus could prevent hazardous exposure to a needle via one-handed operation. It would be highly desirable if the safety shield apparatus could be irreversibly locked to prevent hazardous exposure and provide tactile feedback to indicate activation thereof. It is contemplated that the safety shield apparatus is easily and efficiently manufactured.

SUMMARY

Accordingly, a safety shield apparatus is provided that reduces the occurrence of contaminated needlestick injuries and reduces exposure to pathogens for overcoming the disadvantages and drawbacks of the prior art. Desirably, the safety shield apparatus prevents hazardous exposure to a needle via one-handed operation. Most desirably, the safety shield apparatus irreversibly locks to prevent hazardous exposure and provides tactile feedback to indicate activation thereof. The safety shield apparatus is easily and efficiently fabricated.

The safety shield apparatus, in accordance with the principles of the present disclosure, may be employed for fluid administration, including for example, collecting of blood samples, fluid infusion, etc. The safety shield apparatus reduces the occurrence of contaminated needle stick injuries and exposure to pathogens by placing a needle cannula into a safe position via one handed operation. Two handed operation is also contemplated. The needle cannula in the safe position can be irreversibly locked to enhance safety. The safety shield apparatus may be compact and have a non-alarming tactile feedback indicating activation thereof.

In one embodiment, the safety shield apparatus has: 1) an as shipped position, where the safety shield apparatus is in a ready to use position but covered with a protective sheath; 2) an in use position where the safety shield apparatus remains in the as shipped condition with the sheath removed; and 3) a safe position where the needle is completely contained within the body of the safety shield apparatus. In the safe position, the safety shield apparatus can be irreversibly locked. The safety shield apparatus benefits from several advantages, as will be discussed. It is contemplated that a user may selectively activate the safety shield apparatus to initiate retraction of a needle.

In another embodiment, in accordance with the principles of the present disclosure, a safety shield apparatus is provided that includes a housing extending from a proximal end to a distal end. The housing defines a cavity in a side wall thereof. The distal end of the housing includes a cover having a movable tab. A hub is disposed for movement within the housing. The hub includes a needle having a distal end and a movable projection.

The hub is biased between an extended position, such that the distal end of the needle is exposed and the movable projection is releasably disposed with the cavity, and a retracted position whereby the distal end of the needle is disposed within the housing. The movable tab is engageable with the movable projection to release the movable projection from the cavity to facilitate movement of the hub to the retracted position. This configuration advantageously includes single-handed activation. The housing may be substantially rigid. Further, the needle can be completely contained to prevent exposure to the end and sides of the needle, thereby reducing the opportunity for exposure to blood born pathogens. Desirably, the components of the safety shield apparatus are not exposed and are contained within the housing after activation to avoid defeat of the lockout mechanism. The housing may be monolithically formed.

The proximal end of the housing may define a groove circumferentially disposed about an inner surface thereof that is configured for fixed engagement with the projections. The safety shield apparatus may be disposable and/or discarded after use.

The hub may define a plurality of movable projections that are disposable within a plurality of cavities of the housing. The movable projection may pivotably extend from the hub and is biased radially outward. The cover may have a plurality of movable tabs that are engageable with the plurality of movable projections. The movable tab may extend from the cover for pivotable movement relative thereto. The proximal end of the housing can define a groove on an inner surface thereof that is configured for fixed disposal of the movable projection, in the retracted position.

Alternatively, the cover is separately formed and mounted to the distal end of the housing. The cover can be mounted with the distal end of the housing such that a fluid chamber is formed therebetween. The fluid chamber may define a pocket that accumulates contaminated fluids from the exterior of the needle. The fluid chamber can be defined with a larger outside opening on the cover and a smaller inside opening on the housing. Thus, the needle only contacts the inside opening. Any fluid scraped off the exterior of the needle is contained in the pocket.

In an alternate embodiment, the cover has a plurality of tabs pivotably extending therefrom. The cover may include a wing extending therefrom for manipulation of the housing. Further, the tabs and projections may be disposed behind the needle in an ergonomic configuration, when the needle hub is in the extended position, such that the activating hand of a practitioner stays behind the needle. The tabs and projections may also be disposed proximally relative the wings. This feature allows the hands of the practitioner to be positioned behind the wings and not repositioned or placed over an unprotected needle.

The hub may be biased for movement within the housing via a biasing member, such as, for example, a coil spring supported between the hub and the distal end of the housing, and disposed about the needle. This feature allows the ability to automatically extract the needle and minimize the time an exposed needle may be contacted. The biasing member may also be employed to prevent distal movement of the needle hub in the retracted position.

In an alternate embodiment, the distal end of the housing includes a rigid transverse wall that defines an opening for passage of the needle. The transverse wall further defines a lip that is disposed about the opening and configured to capture the distal end of the needle, in the retracted position. The opening can be configured for engagement with the needle hub to provide stability during operation of the safety shield apparatus. The hub can define an angled distal surface that engages a biasing member disposed between the hub and the distal end of the housing such that, in the retracted position, the hub orients the needle out of axial alignment with the housing and into capture with the lip. The non-alignment of the needle may also provide increased difficulty when attempts are made to defeat locking of the safety shield apparatus.

Further, this configuration traps the tip of the needle behind a rigid wall and under a lip thereby increasing the force required to overcome a safe condition. The needle may be forced into this position by creating an angled surface on the face of the hub. This angled surface will bias the cannula to one side due to pressure applied by the spring. The mounting of the needle in the hub in a non-axial orientation may also provide this effect. This configuration results in a non-axial needle alignment that may reduce stress on the puncture site by allowing the wing set to lay flatter when taped down. The structure of non-alignment between the needle and the housing will make attempts to defeat the safety features difficult. In one embodiment employing non-axial alignment, the needle is aligned with a longitudinal axis of the housing in the extended position. In the retracted position, the needle hub orients the needle out of axial alignment with the housing. In another embodiment employing non-axial alignment, the needle hub orients the needle out of axial alignment with the housing in both the extended and retracted positions.

In another alternate embodiment, the safety shield apparatus includes a housing extending from a proximal end to a distal end and defining a pair of cavities that are diametrically disposed in a side wall of the housing. A cover is mounted to the distal end of the housing and forms a fluid chamber therewith. The cover has a pair of diametrically disposed tabs pivotably extending therefrom. The cover includes a pair of diametrically disposed wings extending therefrom. A hub is disposed for slidable movement with the housing and includes a needle having a distal end extending therefrom. The hub further includes a pair of diametrically disposed projections moveable relative to the hub. The hub is biased for movement within the housing, via a coil spring supported between the hub and the distal end of the housing and disposed about the needle, between an extended position, such that the distal end of the needle is exposed and the projections are each releasably disposed within a corresponding cavity, and a retracted position whereby the distal end of the needle is disposed within the housing. Each of the tabs are engageable with a corresponding projection to release the projection from the cavities such that the coil spring forces the hub to the retracted position whereby the projections are fixedly disposed within a groove formed in the proximal end of the housing.

Thus, by manipulating the safety shield apparatus to squeeze the opposing tabs and projections, some of the safety features that enclose the needle in the housing are activated. The opposing tabs and projections can be simultaneously depressed to provide protection against false activation. The opposing position of the tabs and projections provides a comfortable natural motion to activate the safety features. This pinching motion limits the unbalanced forces on and the movement of the needle that might result in discomfort of injury at the puncture site.

Alternatively, the safety shield apparatus includes a two-stage button, an outer button of the cover is allowed to move the distance of a designed gap before engaging a compressible bump of the hub. This further protects against false activation due to inadvertent engagement. This reduces sensitivity of the safety shield apparatus. The cover button provides concealment for the needle after activation. An additional feature is an easily accessible larger outer surface, when depressed, projects into the cavity to dislodge the hub. This configuration facilitates uniform and reliable activation.

The safety shield apparatus further includes tubing that has a first end attached to a proximal end of the hub and is in fluid communication with the needle. A second end of the tubing is attached to a fluid administration apparatus and is in fluid communication therewith. The safety shield apparatus may include transparent materials so that the practitioner can observe flash back to verify the proper location of the needle. Further, the hub may create a drag with the inner surface of the housing during sliding engagement therebetween to slow activation such that alarming noise and recoil may be controlled.

In an alternate embodiment, a method of use for the safety shield apparatus is provided. The method includes the steps of removing the safety shield apparatus from a package; attaching distal connectors on intravenous tubing connected to the safety shield apparatus to an appropriate circuit of a fluid administration apparatus; removing a sheath from the safety shield apparatus; inserting a needle into a vessel using techniques, such as, for example, a two winged technique, a single wing technique, housing grip technique, etc. In an alternate embodiment, the method may further include any or all of the following steps: taping down the safety shield apparatus; performing blood draw or infusion; removing tape; placing absorbent material over the injection site with one hand, positioning a second hand to remove the safety shield apparatus. Activation of the safety shield apparatus may be used to extract a needle from a patient, or after the needle is extracted from the patient but before being transported or discarded. Activation of the safety shield apparatus may be initiated by pinching opposing buttons between the thumb and finger causing compressible bumps on the hub to be dislodged from a retaining stop of the housing. A spring will then force the hub, cannula and transfer tubing rearward until the compressible bumps are forced into a receiving locking feature creating a locked condition.

BRIEF DESCRIPTION OF THE DRAWINGS

The objects and features of the present disclosure, which are believed to be novel, are set forth with the particularity in the appended claims. The present disclosure, both as to its organization and manner of operation, together with further objectives and advantages, may be best understood by reference to the following description, taken in connection with the accompanying drawings, which are described below.

FIG. 6 is a perspective cross section view of the safety shield apparatus shown in FIG. 2;

FIG. 7 is a perspective view of the indicated area of detail of the safety shield apparatus shown in FIG. 6;

FIG. 14 is an enlarged perspective view of an alternate embodiment of the safety shield apparatus shown in FIG. 1; and FIG. 15 is an enlarged perspective view of another alternate embodiment of the safety shield apparatus shown in FIG. 1.

DETAILED DESCRIPTION OF EXEMPLARY EMBODIMENTS

Figure 1:
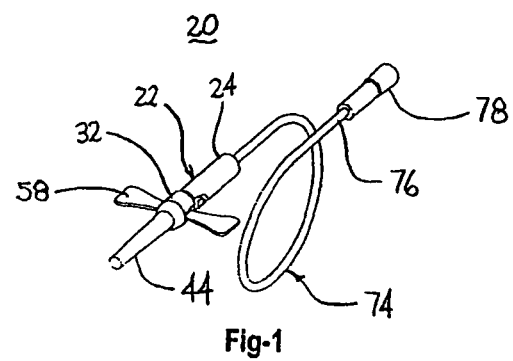
FIG. 1 is a perspective view of one embodiment of a safety shield apparatus, in accordance with the principals of the present disclosure, with a protective sheath.

The exemplary embodiments of the safety shield apparatus and methods of operation disclosed are discussed in terms of medical needle assemblies for the administration of fluids, and more particularly in terms of a safety shield apparatus that prevents hazardous exposure to a needle. It is contemplated that the needle may be shielded during use including storage, transport, fluid infusion and/or collection, subsequent thereto, etc. It is further contemplated that the safety shield apparatus reduces the occurrence of contaminated needle stick injuries and reduces exposure to pathogens. It is envisioned that the present disclosure, however, finds application with a wide variety of cannula needle devices for the infusion of preventive medications, medicaments, therapeutics, etc., as well as injections employed during procedures relating to phlebotomy, orthopedic, digestive, intestinal, urinary, veterinary types, etc., to a subject. It is also envisioned that the present disclosure may be employed for collection of body fluids including those employed during procedures relating to phlebotomy, digestive, dialysis, intestinal, urinary, veterinary, etc. It is contemplated that the safety shield apparatus may be utilized with other medical needle applications including dental, phlebotomy devices, catheters, catheter introducers, guidewire introducers, spinal, epidural biopsy, aphaeresis, dialysis, blood donor, veress needles, Huber needles, etc. The safety shield apparatus may include winged intravenous needle assemblies.

In the discussion that follows, the term "proximal" refers to a portion of a structure that is closer to a practitioner and a term "distal" refers to a portion that is further from the practitioner. As used herein the term "subject" refers to a patient that receives infusions or has blood and/or fluid collected therefrom using the safety shield apparatus. According to the present disclosure, the term "practitioner" refers to an individual administering an infusion, performing fluid collection, install or removing a safety shield apparatus and may include support personnel.

The following discussion includes a description of the safety shield apparatus, followed by a description of an exemplary method of operating a safety shield apparatus in accordance with the principals of the present disclosure. Reference will now be made in detail to the exemplary embodiments and disclosure, which are illustrated with the accompanying figures.

The component parts of the safety shield apparatus are fabricated from materials suitable for medication injections, such as, for example, polymerics or metals, such as stainless steel, depending on the particular medical needle application and/or preference of a practitioner. Semi-rigid and rigid polymerics are contemplated for fabrication, as well as resilient materials, such as molded medical grade polypropylene. The safety shield apparatus may include transparent materials so that a practitioner can observe flash back to verify the proper location of a needle. One skilled in the art, however, will realize that other materials and fabrication methods suitable for assembly and manufacture, in accordance with the present disclosure, also would be appropriate.

In the figures, like components are designated by like reference numerals throughout the several views. Referring initially to FIGS. 1-5, there is illustrated a safety shield apparatus 20, constructed in accordance with the principals of the present disclosure. A housing 22 extends from a proximal end 24 to a distal end 26 and defines a cavity, such as, for example hub retention opening 28 in a sidewall 30 of housing 22. Housing 22 may include one or a plurality of cavities. Distal end 26 includes a cover 32 having a movable tab such as, for example, outer button 34. Cover 32 may include one or a plurality of movable tabs.

A needle hub 36 is disposed for movement within housing 22. Needle hub 36 includes a needle cannula 38 having a distal end 40 and a movable projection, such as, for example, compressible bumps 42 (See FIGS. 5-5B). Needle hub 36 may include one or a plurality of movable projections. Needle hub 36 is biased between an extended position (FIG. 2), such that distal end 40 of needle cannula 38 is exposed and compressible bumps 42 are releasably disposed within hub retention opening 28, and a retracted position (FIG. 3) whereby distal end 40 is disposed within housing 22. Outer button 34 is engageable with compressible bumps 42 to release compressible bumps 42 from hub retention opening 28 of housing 22 to facilitate movement of needle hub 36 to the retracted position. This configuration of safety shield apparatus 20 advantageously reduces the occurrence of contaminated needlestick injuries and reduces exposure to pathogens via one-hand operation, as will be discussed, although two handed use is also contemplated. Further, needle cannula 38 can be completely contained in housing 22 to prevent exposure to the end and sides of needle cannula 38, thereby reducing the opportunity for exposure to, for example, blood born pathogens, etc.

Safety shield apparatus 20 may include an as shipped position (FIG. 1) wherein needle hub 36 (FIG. 4) is in an extended position and ready for use with a sheath 44 releasably mounted thereto and enclosing distal end 40 of needle cannula 38. It is contemplated sheath 44 may fully enclose, partially enclose distal end 40, or alternatively, that safety shield apparatus 20 does not include sheath 44. Safety shield apparatus 20 may include an in use position (FIG. 2), similar to the as shipped position with sheath 44 removed, and a safe position (FIG. 3) wherein needle hub 36 is in the retracted position. It is envisioned that safety shield apparatus 20 may be disposable.

Referring to FIGS. 6 and 7, in one embodiment housing 22 is elongated and defines a pair of diametrically opposed hub retention openings 28. Housing 22 is substantially transparent and is fabricated from a substantially rigid material. Housing 22 may be monolithically formed. It is contemplated that housing 22 may extend variable lengths and have various cross-sectional configurations, such as, for example, circular, polygonal, elliptical, etc. It is further contemplated that housing 22 may be substantially transparent or opaque and formed of a semi-rigid or flexible material, according to the requirements of a particular medical needle application.

Hub retention openings 28 have a generally parabolic configuration and are dimensioned for releasable disposal of compressible bumps 42 therein. Hub retention openings 28 include an inward distal stop 46 (FIG. 7). Upon disposal of compressible bumps 42 within hub retention openings 28, distal stop 46 defines a clearance with compressible bumps 42 therebetween.

Hub retention openings 28 taper radially outward from inward distal stop 46 to outward proximal end 48. Outward proximal end 48 is configured to engage and releasably capture compressible bumps 42 as bumps 42 become disposed within hub retention openings 28. Outward proximal ends 48 are disposed sufficiently radially outward such that, subsequent to capture of compressible bumps 42, bumps 42 may be deflected radially inward and released from engagement with outward proximal ends 48. This releasable configuration advantageously facilitates activation of safety shield apparatus 20 to the safe position via one handed operation.

It is envisioned that hub retention openings 28 may have various configurations and dimensions according to the requirements of a particular medical needle application. It is further envisioned that distal stop 46 and proximal end 48 may be disposed at various radial depths and configurations of hub retention openings 28, including no radial offset of distal stop 46 relative to proximal end 48. Hub retention openings 28 may be variously disposed along the length of housing 22. Housing 22 defines a rolled edge 49 adjacent proximal end 24. Rolled edge 49 may be formed during manufacture of safety shield apparatus 20 and advantageously eliminates the need for additional components to assemble safety shield apparatus 20.

Figure 8:
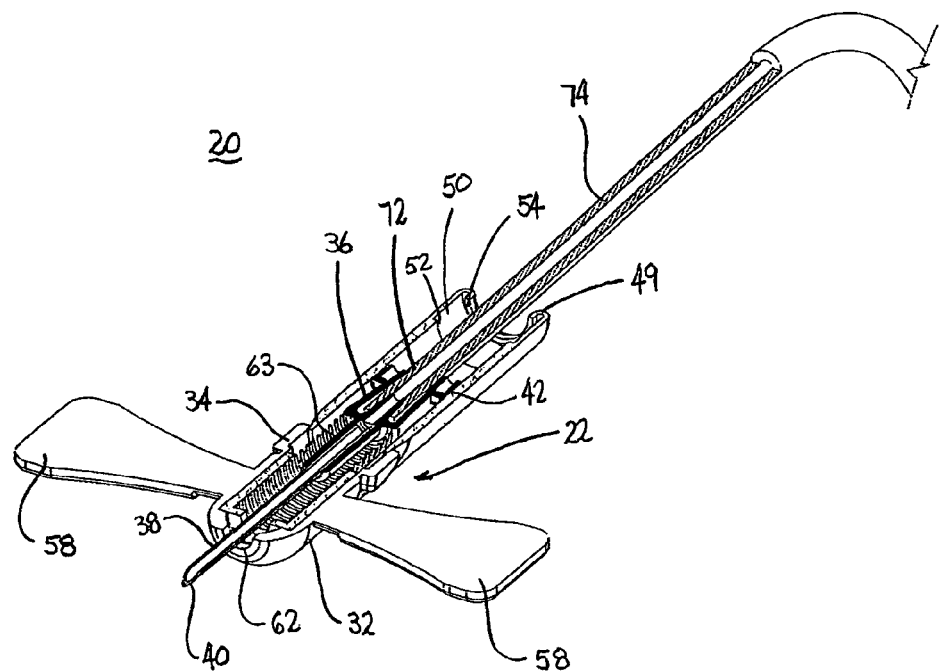
FIG. 8 is a perspective cross section view of the safety shield apparatus during movement to the retracted position.
Figure 9:
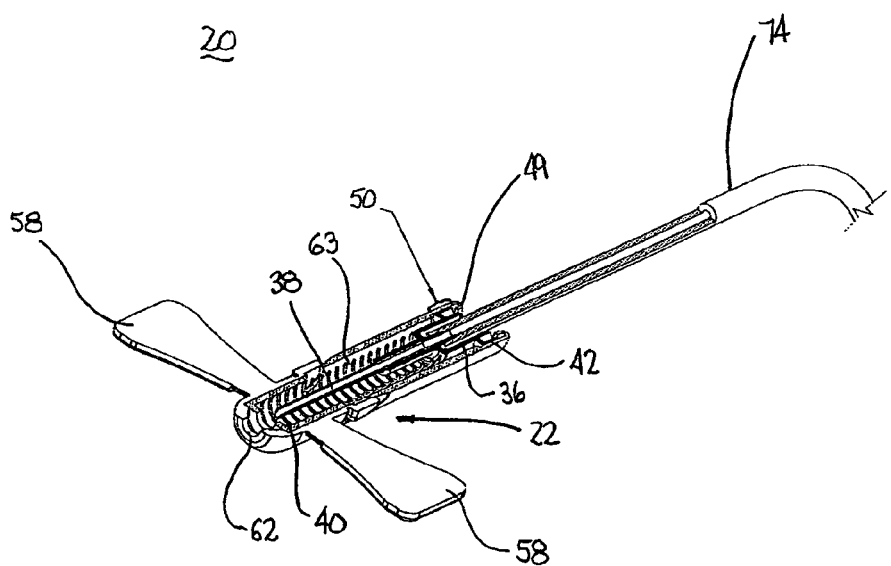
FIG. 9 is a perspective cross section view of the safety shield apparatus shown in FIG. 3.

Referring also to FIGS. 8 and 9, housing 22 defines a groove 50 (FIG. 6) adjacent proximal end 24. Groove 50 is circumferentially disposed about the inner surface of housing 22 and is configured for fixed disposal of compressible bumps 42, in the retracted position (FIG. 9). Groove 50 is recessed within the inner surface of housing 22 and defines a distal stop 52. Distal stop 52 projects radially inward from groove 50 such that upon disposal of compressible bumps 42 within the groove 50, bumps 42 engage distal stops 52 to irreversibly lock needle hub 36 in the retracted position.

Groove 50 includes a proximal stop 54, similar to distal stop 52, that engages compressible bumps 42. Distal stop 52 prevents distal movement of needle hub 36 and proximal stop 54 prevents proximal movement, to facilitate irreversible locking of safety shield apparatus 20 and prevent hazardous exposure of distal end 40 of needle cannula 38. The components of safety shield apparatus 20 are not exposed and are contained within housing 22 after activation to avoid defeat of the lockout mechanism provided by groove 50.

It is contemplated that groove 50 may extend about the entire circumference of housing 22 or only a portion thereof. It is further contemplated that groove 50 may be configured for releasable locking with needle hub 36 or that safety shield apparatus 20 does not include locking groove 50. Groove 50 may be monolithically formed with housing 22 or integrally mounted therewith via separate structure that may include clips, bands, etc. Groove 50 may be variously disposed about the length of housing 22.

Referring to FIGS. 6-9, cover 32 is separately formed and mounted to distal end 26 of housing 22. Outer buttons 34 pivotably extend from cover 32 in a distal direction. Outer buttons 34 are diametrically disposed on cover 32 corresponding to hub retention openings 28. Outer buttons 34 are oriented to overlap compressible bumps 42, disposed within hub retention openings 28, and in substantial alignment with openings 28. Outer buttons 34 define inner surface 56 that conforms to the configuration of the outer surface of compressible bumps 42. It is contemplated that all or portions of cover 32 may be monolithically formed with housing 22. In an alternate embodiment of safety shield apparatus 20, as shown in FIG. 14, cover 32' is monolithically formed with housing 22'.

Outer buttons 34 are engageable to pivot relative to cover 32 and correspondingly engage compressible bumps 42. This interactive configuration causes compressible bumps 42 to deflect radially inward and release from capture with hub retention opening 28, as discussed, to facilitate disposal of safety shield apparatus 20 in the safe position.

Upon release of compressible bumps 42 from hub retention openings 28, outer buttons 34 are free to pivot outwardly and do not interfere with axial movement of needle hub 36. This configuration requires engagement or depression of both opposing outer buttons 34. This advantageously prevents false activation due to, for example, inadvertent engagement of a single button 34. This structure also avoids axial disturbance of safety shield apparatus 20 that may disturb needle cannula 38 at the puncture site, which may result in discomfort or injury to a subject.

It is envisioned that outer buttons 34 may be variously configured and dimensioned. It is further envisioned that the safety features of safety shield apparatus 20 may be employed by depressing a single button or a plurality of buttons. Outer buttons 34 may be planar, tapered, etc. for engagement with compressible bumps 42.

Outer buttons 34 are configured to pivot through the radial gap defined between distal stop 46 and proximal end 48 of hub retention opening 28, further preventing false activation of safety shield apparatus 20. Alternatively, outer buttons 34 move the distance of the gap before engaging compressible bumps 42. This further protects against false activation due to inadvertent engagement and reduces sensitivity of safety shield apparatus 20.

Outer buttons 34 enclose hub retention openings 28 after movement of needle hub 36 to the retracted position, further concealing needle cannula 38 and preventing hazardous exposure. Outer buttons 34 provide concealment for needle cannula 38 after activation. Outer button 34 may have an easily accessible larger outer surface that, when depressed, projects into hub retention opening 28 to dislodge needle hub 36. This configuration facilitates uniform and reliable activation. It is contemplated that outer buttons 34 may not be required. For example, in an alternate embodiment of safety shield apparatus shown generally as 120, as shown in FIG. 15, housing 122 does not include outer buttons. As such, compressible bumps 142 are directly engageable for release from hub retention openings 128 to activate safety features of safety shield apparatus 120, as discussed herein.

Referring again to FIGS. 6-9, cover 32 includes wings 58 that extend laterally therefrom to facilitate manipulation of safety shield apparatus 20. Outer buttons 34 and compressible bumps 42 may be disposed behind needle cannula 38, such that when needle hub 36 is in the extended position, the activating hand of a practitioner remains positioned behind needle cannula 38. This feature allows the hands of the practitioner to be positioned behind wings 58 and not repositioned or placed over an unprotected needle cannula 38.

Wings 58 may pivotably extend from housing 22 and/or be fabricated from a flexible material. It is contemplated that one or a plurality of wings 58 may be employed. It is further contemplated that wings 58 may be variably configured and dimensioned, or alternatively, that safety shield apparatus 20 may not include wings, according to the requirements of a particular medical needle application. Wings 58 may be variously disposed about the length of housing 22.

Figure 4:
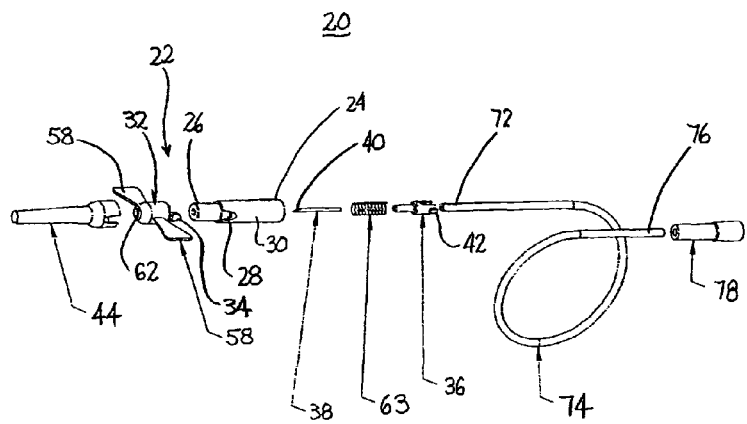
FIG. 4 is a perspective view of the safety shield apparatus shown in FIG. 1, with parts separated.
Figures 5, 5A, 5B:
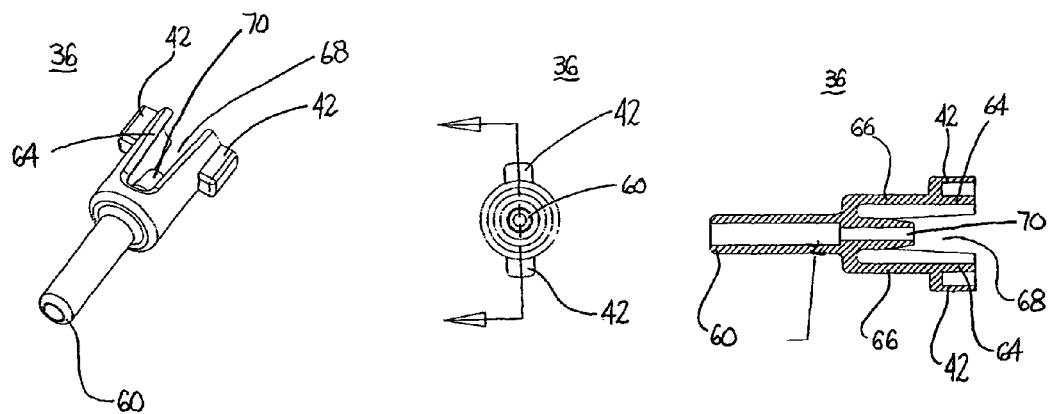
FIG. 5 is a perspective view of a hub of the safety shield apparatus shown in FIG. 1.
FIG. 5A is a front view of the hub shown in FIG. 5.
FIG. 5B is a cross-sectional view taken along section lines 5B-5B of FIG. 5A.

Referring also to FIGS. 4-5B, needle hub 36 is disposed for slidable movement with housing 22. Needle cannula 38 is mounted to a distal end 60 of needle hub 36 and extends therefrom in a distal direction. Distal end 40 of needle cannula 38 extends through an opening 62 formed in cover 32 of housing 22 for employment during a medical needle application.

A coil spring 63 is mounted within housing 22 to facilitate axial relative movement of housing 22 and needle hub 36. Coil spring 63 engages distal end 60 and a surface of housing 22. Coil spring 63 is compressed when needle hub 36 is in the extended position and generates a resilient spring force that biases needle hub 36 to the retracted position. This feature of coil spring 63 allows safety shield apparatus 20 to automatically extract needle cannula 38 from a patient and minimize the time needle cannula 38 may be hazardously exposed. It is envisioned that needle hub 36 may create a drag with the inner surface of housing 22 during sliding engagement therebetween to slow activation such that alarming noise and recoil may be controlled. In the retracted position, coil spring 63 prevents distal movement of needle hub 36 to prevent re-exposure of distal end 40 of needle cannula 38, thereby avoiding a hazardous condition. It is contemplated that distal stop 46 may be configured to engage compressible bumps 42 and prevent distal movement of needle hub 36.

Referring to FIGS. 5-5B, compressible bumps 42 are diametrically disposed about a proximal portion 64 of needle hub 32 and pivotably extend therefrom. Compressible bumps 42 project radially outward from opposing cantilever members 66 of needle hub 36. Cantilever members 66 extend in a proximal direction from needle hub 36 and are flexible such that compressible bumps 42 are biased radially outward. As compressible bumps 42 are depressed radially inward, a resilient spring force is generated in cantilever members 66 causing a resilient bias of compressible bumps 42 radially outward. This configuration facilitates disposal of compressible bumps 42 within for example, hub retention openings 28 and groove 50.

Thus, by manipulating safety shield apparatus 20 to squeeze or pinch the opposing outer buttons 34 and compressible bumps 42, some of the safety features that enclose needle cannula 38 in housing 22 are activated. The opposing outer buttons 34 and compressible bumps 42 can be simultaneously depressed to provide protection against false activation by depressing only a single button 34 and bump 42. The opposing position of outer buttons 34 and compressible bumps 42 provides a comfortable, natural motion to activate the safety features. This "pinching" motion also does not require the user to force the safety shield apparatus to move rearward in a manner that could cause further discomfort or injury at the puncture site. Activation of opposing outer buttons 34 and compressible bumps 42 may be alternatively facilitated by axial force, flip switch, etc.

Cantilever members 66 cooperate to define a hub cavity 68. An extension 70 projects proximally within hub cavity 68 for connection to a first end 72 of transfer tubing 74. Transfer tubing 74 provides a flexible fluid path in fluid communication with needle cannula 38. Transfer tubing 74 is substantially transparent to facilitate visualization of fluid flow therein, such as, for example, flashback.

A second end 76 of transfer tubing 74 is attached with a luer connector 78. Luer connector 78 is attached to a fluid administration apparatus (not shown) that is in fluid communication with needle cannula 38 via transfer tubing 74. Luer connector 78 facilitates interface with a variety of fluid circuits. It is contemplated that safety shield apparatus 20 may be employed with various fluid administration apparatus such as, for example, syringes, dental devices, phlebotomy devices, catheters, catheter introducers, guidewire introducers, biopsy devices, dialysis devices, etc.

Figure 10:
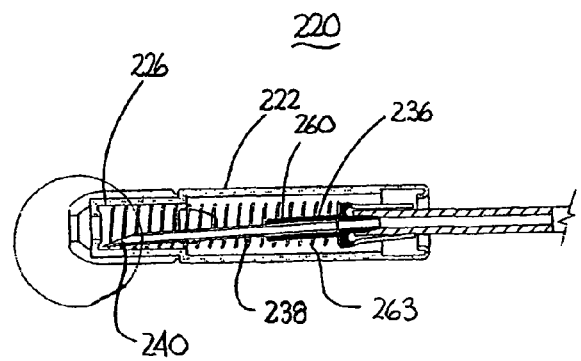
FIG. 10 is a side cross section view of an alternate embodiment of the safety shield apparatus shown in FIG. 9.
Figure 11:
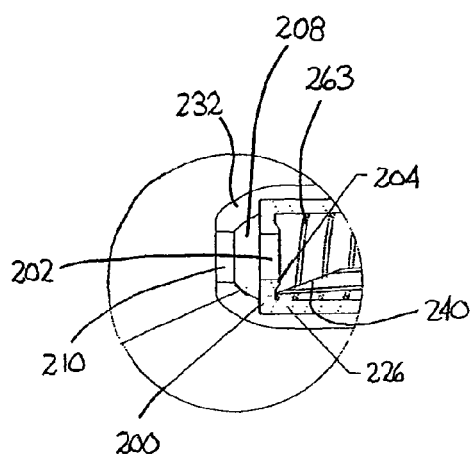
FIG. 11 is an orthographic sectional detail view of the indicated area of detail of the safety shield apparatus shown in FIG. 10.
Figure 12:
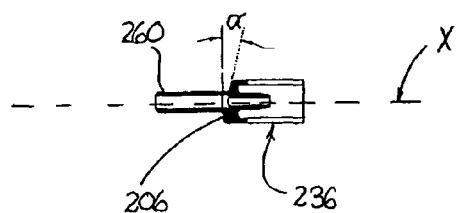
FIG. 12 is a side cross section view of the hub shown in FIG. 10.

Referring to FIGS. 10-12, an alternate embodiment of the presently disclosed safety shield apparatus shown generally as 220 is shown. Distal end 226 of housing 222 includes a rigid transverse wall 200 that defines an opening 202 for passage of needle cannula 238. Transverse wall 200 further defines a circumferential lip 204 disposed about opening 202. Lip 204 is configured to capture distal end 240 of needle cannula 238, in the retracted position of needle hub 236, as shown in FIG. 10. It is contemplated that lip 204 may be disposed about all or, alternatively, only a portion of opening 202. Opening 202 is configured to receive and slidably support needle hub 236. The surface of opening 202 engages distal end 260 of needle hub 236 to advantageously provide stability during operation of safety shield apparatus 220.

Capturing distal end 240 of needle cannula 238 behind transverse wall 200 and lip 204, relative to opening 202, prevents exposure of distal end 240 by increasing the force required to overcome the safe condition of safety needle apparatus 220, as shown in FIG. 10.

Needle cannula 238 is oriented into a position for capture of distal end 240 due to the configuration of needle hub 236. Needle hub 236 defines an angled distal surface 206 (FIG. 12). Distal surface 206 is oriented at an angle a, which is measured from a plane transverse to a longitudinal axis x of safety shield apparatus 220. It is envisioned that angle a may include various degrees of inclination, according to the requirements of a particular medical needle application. Other structure may be employed with safety shield apparatus 220 for orienting needle cannula 238 into a capture position, such as, for example, pivot structure, ball joint, etc.

Figure 13:
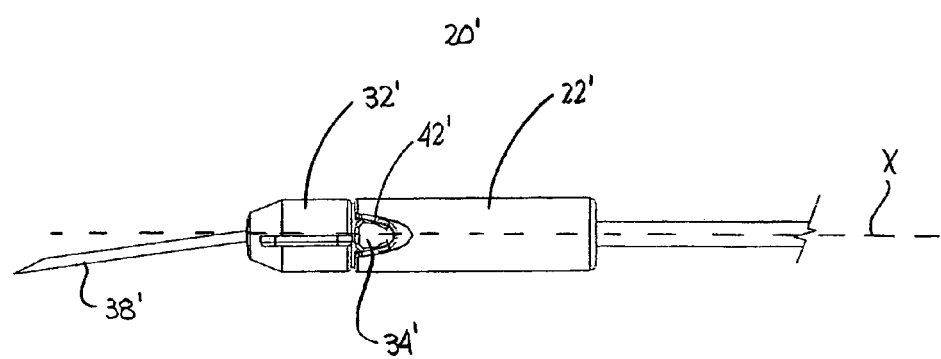
FIG. 13 is a side view of the safety shield apparatus shown in FIG. 10, in the extended position.

In the extended position (not shown), needle cannula 238 extends from housing 222 and orients needle cannula 238 in substantial alignement with longitudinal axis x of housing 222. Coil spring 263 engages angled distal surface 206 and the inner surface of housing 222. Coil spring 263 is compressed and generates a resilient spring force that biases needle hub 236 to the retracted position, similar to that discussed. In an alternate embodiment, as shown in FIG. 13, a safety shield apparatus 20' is in the extended position. In the extended position, needle cannula 38' extends from housing 22' and orients needle cannula 38' out of alignment with longitudinal axis x of housing 22'. This configuration results in a non-axial needle alignment that reduces stress on the puncture site of a subject by allowing safety shield apparatus 20' to lay flatter when taped down to the subject.

Outer buttons 34' and compressible bumps 42' are manipulated to activate some of the safety features of safety shield apparatus 20', as discussed above, and the needle hub (not shown) is forced to the retracted position. In the retracted position, similar to that shown in FIG. 10, a coil spring 263 engages transverse wall 200 and angled distal surface 206 on needle hub 236 to orient needle cannula 238 out of axial alignment with longitudinal axis x of housing 222 and into capture with lip 204.

Angled distal surface 206 biases needle cannula 238 toward side wall 230 of housing 222 due to pressure applied to surface 206 from coil spring 263. It is contemplated that needle cannula 238 may be mounted with needle hub 236 at an inclination that directs distal end 240 toward side wall 230. Other structures that incline distal end 240 behind lip 204 are also contemplated. The non-alignment of needle cannula 238 advantageously provides increased difficulty when attempts are made to defeat locking of safety shield apparatus 220.

Cover 232 is mounted to distal end 226 of housing 222 such that a fluid chamber 208 is formed therebetween. Fluid chamber 208 is configured to contain fluid and may be variously dimensioned according to the requirements of a particular medical needle application. As shown in FIG. 11, the fluid chamber 208 is configured to have a width greater than the width of opening 202, such that the cover 232 contains fluid within fluid chamber 208. For example, contaminated fluids may accumulate on the outer surface of needle cannula 238. Fluid chamber 208 facilitates containment by collecting such fluids from the outer surface of needle cannula 238. Cover 232 defines an opening 210 that is larger in diameter than opening 202. Openings 210 and 202 define opposite sides of fluid chamber 208. Opening 202 is smaller than opening 210 such that needle cannula 238 only engages opening 202. Thus, fluid is scraped from needle cannula 238 by the edges of opening 202 and collects in fluid chamber 208.

Referring again to FIGS. 1-3, safety shield apparatus 22, similar to that described above, is assembled, sterilized and packaged for use. In operation, safety shield apparatus 20 is removed from a package. First end 72 of intravenous transfer tubing 74 is connected to extension 70 of safety shield apparatus 20. Second end 76 of tubing 74, including luer connector 78, is connected to an appropriate fluid circuit of a fluid administration apparatus (not shown). Sheath 44 is removed from safety shield apparatus 20.

Needle cannula 38 is inserted into a vessel (not shown) of a subject and a medical needle procedure is performed to completion. Safety shield apparatus 20 may be taped down onto the subject and removed upon completion of the medical needle procedure. It is envisioned that upon completion of the medical needle procedure the practitioner places absorbent material over the injection site with one hand and positions a second hand to grasp wings 58 for removal of safety shield apparatus 20.

Figure 2:
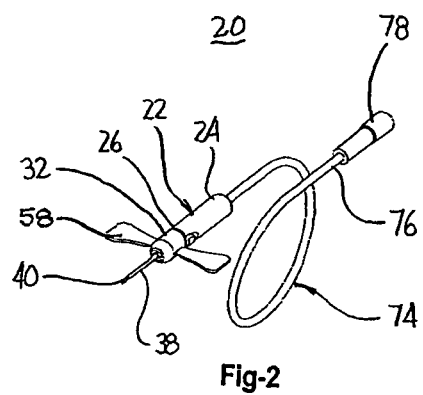
FIG. 2 is a perspective view of the safety shield apparatus shown in FIG. 1, in the extended position with the sheath removed.
Figure 3:
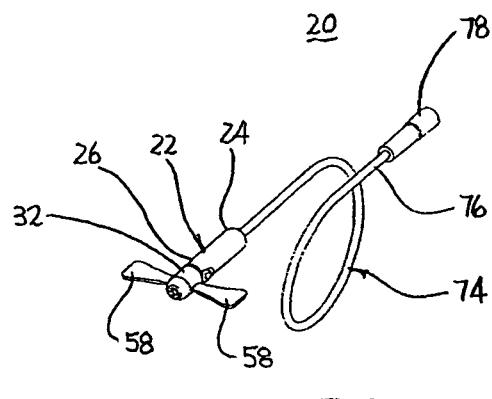
FIG. 3 is a perspective view of the safety shield apparatus shown in FIG. 1, in the retracted position.

Safety shield apparatus 20 extracts needle cannula 38 from the subject and needle hub 36 is in the retracted position, as shown in FIGS. 2 and 6. The safety features of safety shield apparatus 20 are initiated by pinching opposing out buttons 34 between a thumb and finger of the practitioner causing compressible bumps 42 on needle hub 36 to dislodge from hub retention openings 28 of housing 22, as discussed and shown in FIG. 8. Coil spring 63 forces needle hub 36, needle cannula 38 and transfer tubing 74 proximally until the locking features of safety shield apparatus 20, discussed above, are activated, and create an irreversibly locked or safe condition, as shown in FIGS. 3 and 9. Safety shield apparatus 20 may be discarded. Other methods of use are also contemplated.

It will be understood that various modifications may be made to the embodiments disclosed herein. Therefore, the above description should not be construed as limiting, but merely as exemplifications of the various embodiments. Those skilled in the art will envision other modifications within the scope and spirit of the claims appended hereto.

What is claimed is:

1. A safety shield apparatus comprising:
a housing defining a longitudinal axis and having a distal end including a substantially transverse wall defining a first opening;
a cover fixedly mounted to the distal end of the housing, the cover defining a second opening, the cover and the housing defining a fluid chamber therebetween having a width wider than the first opening and the second opening; and
a needle cannula supported on a needle hub having a planar distal surface skewed at an angle other than 90 degrees measured from the needle cannula, the needle hub being slidably supported within the housing from an advanced position to a retracted position to move the needle cannula from a first position extending from the housing and cover through the first and second openings to a second position located within the housing;

wherein the second opening is larger in diameter than the first opening, the first opening being dimensioned to scrape fluid from the needle cannula during movement of the needle cannula from its first position towards its second position.

2. The safety shield apparatus according to claim 1, wherein the fluid chamber is positioned to collect the fluid scraped from the needle cannula.

3. The safety shield apparatus according to claim 1, further including a biasing member positioned within the housing to urge the needle cannula toward its second position.

4. The safety shield apparatus according to claim 3, wherein the biasing member is positioned between the transverse wall of the housing and the needle hub.

5. The safety shield apparatus according to claim 4, wherein the biasing member is positioned to engage the skewed distal surface such that when the needle hub moves from the advanced position to the retracted position, the biasing member urges the needle cannula toward a side wall of the housing to move the needle cannula out of alignment with longitudinal axis of the housing.

6. The safety shield apparatus according to claim 5, further including an annular lip formed about the first opening positioned to capture the needle cannula after the needle cannula has been moved to its second position.

7. The safety shield apparatus according to claim 1, wherein the needle cannula is aligned with the longitudinal axis of the housing in its first position.

8. The safety shield apparatus according to claim 1, wherein the needle cannula is misaligned with the longitudinal axis of the housing in its first position.

9. The safety shield apparatus according to claim 1, wherein the needle hub includes at least one movable projection and the housing includes at least one cavity, the at least one movable projection being releasably disposed within the at least one cavity to retain the needle cannula in its first position.

10. The safety shield apparatus according to claim 9, wherein the at least one cavity includes two cavities and the at least one projection includes two projections.

11. A safety shield apparatus comprising:
a housing defining a longitudinal axis and having a distal end including a substantially transverse wall having a first opening;
a needle hub slidably supported within the housing, the hub having a planar distal surface skewed at an angle other than 90 degrees measured from the longitudinal axis of the housing;
a needle supported on the hub; and
a biasing member positioned in the housing engaging the distal surface of the hub to bias the hub from an extended position in which a distal end of the needle extends from the housing to a retracted position in which the distal end of the needle is disposed within the housing.

* * * * *